United States Patent [19]
Vorberg

[11] Patent Number: 5,866,352
[45] Date of Patent: Feb. 2, 1999

[54] KIT FOR FRUCTOSAMINE DETERMINATION

[75] Inventor: Ewald Vorberg, Freiburg, Germany

[73] Assignee: Roche Diagnostic Systems, Inc., Branchburg, N.J.

[21] Appl. No.: 886,799

[22] Filed: Jul. 2, 1997

Related U.S. Application Data

[63] Continuation of Ser. No. 612,595, Mar. 8, 1996, abandoned, which is a continuation of Ser. No. 277,729, Jul. 20, 1994, abandoned.

[30] Foreign Application Priority Data

Jul. 27, 1993 [EP] European Pat. Off. ............... 93111966

[51] Int. Cl.⁶ ..................................................... C12Q 1/26
[52] U.S. Cl. .............................. 435/25; 435/14; 436/175; 436/176; 436/825
[58] Field of Search .................... 435/4, 14, 25; 436/87, 175, 176, 825, 903

[56] References Cited

U.S. PATENT DOCUMENTS

| | | | |
|---|---|---|---|
| 4,613,569 | 9/1986 | Geisler et al. | 435/26 |
| 4,645,742 | 2/1987 | Baker | 436/15 |
| 4,847,196 | 7/1989 | Geisler et al. | 435/26 |
| 4,956,301 | 9/1990 | Ismail | 436/87 |
| 5,002,893 | 3/1991 | Rosenthal | 436/87 |
| 5,055,388 | 10/1991 | Vogt et al. | 435/4 |
| 5,149,633 | 9/1992 | Vogt et al. | 435/25 |
| 5,156,947 | 10/1992 | Seidel et al. | 435/4 |
| 5,288,606 | 2/1994 | Seidel et al. | 435/4 |
| 5,312,759 | 5/1994 | Hama | 436/87 |
| 5,312,760 | 5/1994 | Kwan | 436/87 |

FOREIGN PATENT DOCUMENTS

| | | |
|---|---|---|
| 054 689 | 10/1981 | European Pat. Off. . |
| 085 263 | 8/1983 | European Pat. Off. . |
| 309 882 | 9/1988 | European Pat. Off. . |
| 473 101 | 8/1991 | European Pat. Off. . |
| 473 189 | 8/1991 | European Pat. Off. . |
| 0473101 | 3/1992 | European Pat. Off. . |
| 91/125437 | 11/1992 | Japan . |

OTHER PUBLICATIONS

Johnson, R., Fructosamine: A New Approach to the Estimation of Serum Glycosylprotein. Clinica Chimica Acta 127:87–95, 1982.
Clin. Chem. 1994; 40(6): 1028 Poster Abstract No. 0570 (Presentation at the 46th National Meeting of the AACC, Jul. 17–21, 1994, New Orleans).
Baker, J., Clin. Chem. 37(4):552–556 (1991) "Fructosamine test plus, a modified . . . ".
Kallner, A., Clinica Chimica Acta 207:99–106 (1992) "Influence of triglycerides . . . ".
Derwent Abstract No. AN 92/430307.
Ismail K. Analytical Review in Clinical Biochemistry, Biyokimya Dergisi vol. 18(4), 109–138, 1993.
Baker J., Fructosamine Test–Plus, a Modified Fructosamine Assay Evaluated, Clinical Chemistry, 37/4, 552–556, 1991.
Kallner A., Influence of Triglycerides and Urate on Methods for Determination of Fructosamine, Clinica Chimica Acta 207 99–106.

*Primary Examiner*—Ralph Gitomer
*Attorney, Agent, or Firm*—George W. Johnston; Dennis P. Tramaloni

[57] ABSTRACT

A kit of two liquid reagent components for determining the fructosamine content of a blood sample measured by color change, and methods of determining fructosamine content of a blood sample using these two liquid reagents are disclosed.

10 Claims, No Drawings

KIT FOR FRUCTOSAMINE DETERMINATION

This is a continuation of application Ser. No. 08/612,595 filed Mar. 4, 1996. Now abandoned which is a continuation of application Ser. No. 08/277,729 filed Jul. 20, 1994 now abandoned.

BACKGROUND OF THE INVENTION

An important parameter in monitoring metabolic control in diabetes is a measurement of blood or serum fructosamine. Fructosamine is formed by non-enzymatic glycosylation of proteins by glucose. In addition, since the fructosamine linkages formed by this glycosylation are stable, fructosamine content is much less variable than glucose content. Therefore, fructosamine content is a useful index of the average glucose levels. An accurate means of fructosamine determination as provided by this invention is important in diagnosing and monitoring diabetes.

European Patent Publication No. 85 263 describes a simple method of determining the fructosamine content in serum samples. This method is based on the fact that fructosamines in alkaline solution form eneaminols which act as reducing agents on tetrazolium salts, such as for instance nitro-blue tetrazolium (NBT), thereby causing a change in color which can be photometrically determined, the measured change in color in a defined time interval being proportional to the quantity of fructosamines present in the sample.

This method however has a number of drawbacks. Problems may arise in particular when using serum as sample material, because other serum components, such as bilirubin, uric acid or proteins with free thiol groups also act as reducing agents on the color indicators or reagents. Besides, lipids, when present in high concentration, may cause turbidity of the sample, which has negative effects on photometric measurements and makes determination of the fructosamine content difficult, if not impossible.

To overcome these drawbacks, it has been proposed in European Patent Publication No. 309 882 to treat the sample before the color reaction, at a nearly neutral pH, with reagents which remove the interfering sample components, and then to set a basic pH which is necessary for the color reaction, and start the color reaction by adding the color indicator or reagent. This process is practically carried out with a set of two separate ready to use liquid reagents, the first reagent being an almost neutral buffer, which contains the reagents for removing the interfering sample components, and the second reagent being an alkaline buffer, which contains the color reagent. In order to use this process on automated clinical analysers, the color reagent and the alkaline buffer must be present in a relatively high concentration. It has been found however that the color reagents, usually tetrazolium salts, are not stable in alkaline medium in the presence of relatively high concentrations of color reagent and buffer salts, so that said second reagent is not shelf-stable.

In commercially available kits (Fructosamine Plus and Unimate Fructosamine, Hoffmann-La-Roche, Basel, Switzerland), this disadvantage has been avoided by separating the reagent components as follows: the first reagent consists of a tablet, which contains the color indicator and agents for removing non specifically reducing sample components, such as uricase; the second reagent component consists of an alkaline buffer which contains the remaining agents. In order to make the ready to use solution necessary for the analysis, the tablet (first reagent) must then first be dissolved in the second reagent. This way of proceeding gives excellent results but has following drawbacks: dissolution of the tablet takes at least 15 minutes and cannot be automated; the thus obtained solution of mixed reagents has a usable life time of less than two weeks.

There is therefore a need for reagents for determining the fructosamine content which do not have the above drawbacks. The problem to be solved by the present invention is to provide such reagents. This problem is solved by providing the set of reagents of this invention.

SUMMARY OF THE INVENTION

The invention relates to a kit including separate liquid reagent components for determining the fructosamine content of a blood sample. The first liquid reagent component is at a substantially neutral pH and contains a color indicator capable of being reduced by fructosamine under basic pH conditions and which changes color when so reduced by fructosamine. The first reagent component also contains materials for removing color-interfering components of a sample. The second liquid reagent is at a basic pH and contains a basic buffering agent. Any conventional additional components may also be included.

The present invention also concerns a method of determining the content of fructosamine in a blood sample or a sample derived from blood and the use of the above set of reagents in such a method.

DETAILED DESCRIPTION OF THE INVENTION

By means of the claimed invention, the fructosamine content of a blood sample may be accurately determined by reduction of the color indicator by fructosamine and in the absence of nonspecific reduction and turbidity in the sample, both of which interfere with color determination. In addition, the reagents of this invention are stable as liquids in both use and storage. These results are attained by providing the color indicator at a substantially neutral pH with materials for removing color-interfering components of the sample in a first liquid reagent component, and a basic buffer in a second liquid reagent component.

The expression "fructosamine content" means the total content of stable non enzymatically glycosylated proteins. This parameter, which reflects average blood glucose levels over a period of time, is useful for monitoring metabolic control in diabetes. By blood sample is meant any sample which is blood or is derived from blood. Blood sample includes whole blood, serum, blood products, and any blood fraction which is obtained by processing a blood specimen.

All pH ranges provided herein are inclusive. By substantially neutral pH is meant a pH with a range of from about pH 6 through about pH 9, preferably about pH 7 through pH 8. By basic pH is meant a pH with a range of from about pH 9 through about pH 12.5, preferably about pH 10 through pH 11. The terms basic and alkaline are used interchangeably. Conventional methods of obtaining a desired pH using appropriate conventional buffers may be used to obtain desired pH in the first and second liquid reagent components. Any conventional buffer may be used. The amount of buffer used is sufficient to obtain the desired pH, which may be determined by conventional methods such as a pH meter or test strip.

For example, the first liquid reagent component having a substantially or almost neutral pH may contain an appropriate non reducing buffering agent, usually at a concentration between 10 and 100 mmol/l. This buffering agent is advantageously chosen among buffers having a pH from about 6 through about 9, particularly between about 7 and about 8. A particularly convenient buffering agent is potassium phosphate buffer having a pH from about 7 through about 8.

The second liquid reagent component having a basic pH may contain a basic buffering agent having a pH from about 9 through about 12.5, preferably from about pH 10 through about pH 11. An advantageous buffering agent is potassium phosphate buffer having a pH from about pH 10 through about pH 11, or a carbonate buffer.

Any conventional color indicator which is determined to change color when exposed to fructosamine is useful in this invention. The color change may be detected visually or by conventional photometric methods for determining absorption at an appropriate wavelength. In particular, the color indicator may be a substance capable of being reduced under alkaline pH conditions by the eneaminol form of fructosamine, the reduced form of the color indicator having a color different from that of the non reduced form, so that appearance of the reduced form can be photometrically followed. Numerous examples of such color indicators are found among tetrazolium salts, which in alkaline medium are capable of being reduced to formazans. These salts are well known and can be obtained from conventional sources or produced by known methods (for example Sigma, Aldrich). Examples of such tetrazolium salts are:

- 3,3'-(3,3'-dimethoxy-(1,1'-biphenyl)-4,4'-diyl)-bis(2-(p-nitrophenyl)-5-phenyl-2H-tetrazolium chloride (nitro-blue tetrazolium NBT),
- 3,3'-(3,3'-dimethoxy-(1,1'-biphenyl)-4,4'-diyl)-bis(2,5-bis (p-nitrophenyl)-2H-tetrazolium chloride) (TNTB),
- 3,3'-(1,1'-biphenyl-4,4'-diyl)-bis(2,5-diphenyl-2H-tetrazolium chloride) (NeoTB),
- 3-(p-iodophenyl)-2-(p-nitrophenyl)-5-phenyl-2 H-tetrazolium is chloride (INT),
- 3-(4,5-dimethyl-2-thiazolyl)-2,5-diphenyl-2H-tetrazolium bromide (MTT), and
- 2,5-diphenyl-3-(1-naphthyl)-2H-tetrazolium chloride (TV).

Color indicators are used in an amount such that the color change is detectable visually or photometrically. In particular, tetrazolium salts are preferably used at a concentration between 0.2 and 2 mmol/l in the first liquid reagent. A particularly convenient tetrazolium salt is nitro-blue tetrazolium in a concentration which provides a detectable color change, for example, at a concentration between 0.5 and 1.5 mmol/l in the first liquid reagent.

Color-interfering components of the sample are components in the sample which interfere with the determination of fructosamine content. For example, such components may interfere by reacting with the color indicator, for example by causing nonspecific reduction of the color indicator. Color-interfering components may also interfere by making the sample turbid and making the color change more difficult to measure.

The expression "non specifically reducing components" means here sample components other than fructosamine which, under alkaline pH conditions, are capable of reducing the color indicator. Such components may be bilirubin, uric acid and proteins with free thiol groups, as well as vitamins such as ascorbic acid and pharmaceutical metabolites, such as 2,5-ihydroxybenzoic acid, a metabolite of acetylsalicylic acid. The expression "turbidity-causing components" means non water-soluble blood components such as lipids, which are capable of causing turbidity in samples.

Materials for removing color-interfering components of the sample are any materials which react with such components or their precursors in order to inactivate, degrade, or change such components or in any other way prevent such components from interfering with determination of fructosamine content in this invention. Removal as used herein thus includes prevention. Such materials are used in an amount sufficient to bring about removal. Removal can be determined by conventional methods, for example by adding to a sample a sufficient amount of a material to remove color-interfering components and visually or photometrically comparing the samples before and after addition to determine that a sample is less turbid or does not exhibit color change after addition of the added amount of material.

Materials which remove color-interfering components of the sample include agents which prevent nonspecific reduction and agents which remove turbidity. Thus the first liquid reagent of this invention may contain an agent or agents which prevent nonspecific reduction, or an agent or agents which remove turbidity, or both such agents or groups of agents in any desired combination and in sufficient amounts to prevent reduction or remove turbidity, which amounts may be determined by conventional methods, for example by comparing samples before and after addition of such agents.

Preferred agents for removing non specifically reducing components are enzymes with oxidizing activity such as uricase, bilirubin-oxidase, peroxidase, catalase and/or ascorbic acid oxidase. These enzymes are well known and may be obtained from conventional sources. The enzymes may be stabilized by addition of salts such as potassium chloride. The enzymes may be used in a concentration sufficient to prevent nonspecific reduction. They are preferably used at a concentration between 10 and $10^7$ U/l in the first liquid reagent component of this invention.

Because blood usually contains a substantial amount of uric acid, the latter being the end product of metabolism of purine in man and other primates, uricase, an enzyme which catalyses oxidation of uric acid into allantoin, is especially useful as an agent for removing non specifically reducing components. Uricases may be isolated by conventional methods from sources such as mammalian kidney and liver, and microorganisms such as yeast. Examples of appropriate commercially available uricases are those isolated from *Candida albicans* (Seppim, Sées, 61500, France), *Aspergillus flavus* (Merck), pig liver (Serva, Heidelberg, FRG), *Arthrobacter globiformis* (Sigma), and *Arthrobacter protophormiae* (Boehringer Mannheim). A particularly preferred uricase is uricase of *Arthrobacter protophormiae* which may be used in an amount sufficient to prevent nonspecific reduction, and is preferably used at a concentration between 500 and 1500 U/l in the first liquid reagent component.

Other agents which prevent nonspecific reduction and may be used in the first reagent component are thiol-blocking agents which react with free thiol groups. Such thiol-blocking agents are for instance iodoacetamide, iodoacetate, N-ethylmaleinamide and mercuric p-hydroxybenzoate which may be obtained from conventional sources or produced by known methods. These reagents are used in amounts sufficient to prevent nonspecific reduction, preferably at a concentration between 0.5 and 500 mmol/l, particularly between 5 and 50 mmol/l, in the first liquid reagent component. The preferred thiol-blocking agent is iodoacetamide. Oxidizing enzymes and thiol-blocking agents may be used separately or in any combination as agents to prevent nonspecific reduction in the claimed invention.

Agents which remove turbidity may degrade or sequester turbidity-causing components in the sample when used in sufficient amounts as described. Agents for removing turbidity-causing components include enzymes which catalyse their degradation, such as lipases, as well as anionic, cationic and non ionic detergents, if desired in combination with salts of strong acids. In the first reagent component, such detergents can be used separately or in combination with or without the addition of salt of a strong acid or acids. Lipases may also be included. These enzymes and detergents are obtained from conventional sources, as are salts of strong acids.

Preferred anionic detergents are salts of bile acids and their conjugates with alkali metals and alkaline-earth metals used in sufficient amounts to remove turbidity. Anionic detergents are preferably used at a concentration between 2 and 10 mmol/l in the first liquid reagent component. An interesting such salt is sodium cholate, particularly when used at a concentration between 8 and 16 mmol/l in the first liquid reagent.

A large variety of non ionic detergents may be used in sufficient amounts to remove turbidity. Proper non ionic detergents include in particular linear and branched alkyl- or arylalkyl-alcohol-polyglycolethers with 8 to 12 carbon atoms in the alcohol part and 4 to 15 glycol units per molecule. Examples of such commercially available non ionic detergents are Genapol X-80 (an isotridecylpoly-(ethylenglycolether)$_n$ with n=8, available from Boehringer Mannheim), Oxetal ID 104 (Zschimmer & Schwarz, Lahnstein, FRG), Lutensol ON 50, ON 60, ON 70 (BASF) and Soprofor D/916 (Rhone Poulenc, France) One of such non ionic detergents or a mixture thereof is preferably added at a concentration between 0.05 and 15% in weight, particularly between 0.1 and 5% in weight, in the first liquid reagent component. Isotridecylpoly(ethyleneglycolether)$_n$ is advantageously used, particularly at a concentration between 50 and 110 mmol/l in the first liquid reagent.

The effect of removing turbidity-causing components is stronger in the presence of salts of strong acids, for example, salts of sulfuric acid or hydrochloric acid with an alkali metal or an alkaline-earth metal. Preferred such salts are potassium and sodium chloride. Strong acid salts are preferably used at a concentration between 20 and 200 mmol/l in the first liquid reagent component. Therefore, salts of strong acids in sufficient amounts to enhance the effects of any detergent or combination of detergents may be added to the first reagent of this invention.

The above described set of liquid reagent components has an excellent stability under conditions of storage and of use.

The invention also relates to a method of determining the fructosamine content in a blood sample or a sample derived from blood, by treating the sample with a color indicator and measuring the induced change of color, whereby non specifically reducing and/or turbidity-causing components of the sample are removed during or prior to the color reaction, which method uses the above described liquid reagent components. Therefore, this invention includes a method for determining the fructosamine content in a blood sample. This method comprises mixing the sample with the first liquid reagent component of this invention, which is at a substantially neutral pH and contains a color indicator capable of being reduced by fructosamine under basic pH conditions and which changes color when so reduced, and contains materials for removing color-interfering components of the sample, such that color-interfering materials are removed from the sample. Then the pH of the sample is adjusted to a basic pH of about 9 through about 12.5 by adding the second liquid reagent component of this invention which is at a basic pH and contains a basic buffering agent. At this pH range the color reaction takes place and fructosamine content is then determined by optically measuring the color of the sample and comparing the color change with a calibrator solution, as further described below.

Both the first and second reagent components are used in sufficient amounts to remove color-interfering components and to bring about color change induced by fructosamine content as described (preferred amounts and specific agents used in the first and second reagent components are as described above). This invention also includes a method whereby the first liquid reagent component and the second liquid reagent component are first mixed together, and then the sample is added to the mixture, and the color change measured as described. A further method in which the first liquid reagent component, the second liquid reagent component, and the sample are simultaneously combined and the resulting color change measured, is also part of this invention.

In a preferred embodiment of this method, the sample is first mixed with the above described first reagent in order to remove the interfering components, then the color reaction is started by adding an appropriate quantity of the above described second liquid reagent, so as to adjust the pH of the reaction mixture between about 9 and about 11, preferably between about 10 and about 11. The second reagent is preferably added between 0 and 10 minutes after the sample is mixed with the first reagent.

The rate of change of color of the reaction mixture is photometrically determined at an appropriate wavelength and compared to that of a calibrating solution. Any conventional calibrating solution may be used. Advantageous calibrating solutions are those containing a known concentration of ketoamine, preferably glycated poly-L-lysine (cf. EP 351 790), or deoxymorpholinofructose (DMF), or a serum standardized with one of these calibrators, which can be produced by known methods or obtained from conventional sources. The wave length chosen is usually close to the wave length of maximum of absorption of the reduced form of the color indicator. When the color indicator is nitro-blue tetrazolium the preferred wave length is 550 nm.

In an alternative preferred embodiment of the method, the sample and the above described first and second liquid reagent components are mixed simultaneously.

It is also possible to mix first the above described first and second liquid reagent components and subsequently to add the sample to the mixture of reagents. The second liquid is then preferably used in such an amount as to adjust the pH of the reaction mixture between about 9 and about 11, preferably between about 10 and about 11.

The use of the kit of reagent components of the invention has the advantage, compared to commercial sets of reagents comprising a tablet, that mixing of reagents can be quickly conducted and completely automated.

The present invention will be further illustrated by the following examples, which are not intended to limit the invention.

EXAMPLE 1

Preparation of a Set of Reagents According to the Invention

A set of first and second liquid reagent components according to the invention was prepared with the following composition:

First liquid reagent R1:

1.2 mmol/l nitro-blue tetrazolium (NBT)

4000 U/l uricase of Arthrobacter protophormiae (Boehringer Mannheim)

80 mmol/l isotridecylpoly(ethyleneglycolether)8 (Genapol X-80, Boehringer Mannheim)

12 mmol/l sodium cholate 100 mmol/l potassium phosphate buffer pH 7.5

100 mmol/l potassium chloride

Second liquid reagent R2: 1.5 mol/l potassium carbonate buffer pH 10.4

EXAMPLE 2

Study of the Stability of the Set of Reagents of the Invention

1) Stability of under conditions of storage.

This stability was studied, by measuring the absorption at a wave length of 550 nm and determining the uricase activity (by spectrometrically following, at a wavelength of 293 nm and a temperature of 25° C., the transformation of uric acid in presence of catalase, as recommended by Boehringer Mannheim), for a sample of freshly prepared first liquid reagent R1, a sample of first liquid reagent R1 after one year of storage at a temperature between 2° and 8° C. and a sample of first liquid reagent R1 after one year of storage at a temperature between 24° and 26° C., and by performing the method described in Example 3 under point 1) b) -mode C- with the above samples of reagent R1, and samples of reagent R2 stored in the same conditions, and thereby measuring the photometric linear response maximum concentration and the calibration factor. Two control serum lots and one calibrator lot (human serum containing glycated albumin, standardized with glycated polylysine) were used as samples.

Results are shown in Table 1, hereafter.

TABLE 1

|  | fresh | 1 year 2–8° C. | 1 year 24–26° C. |
|---|---|---|---|
| Absorption at 550 nm | 0.009 | 0.007 | 0.024 |
| % uricase activity compared with freshly prepared R1 | 100 | 105 | 77 |
| Linear response maximum concentration ($\mu$mol/l) | 1251 | 1591 | 1568 |
| Calibration factor | 7754 | 7896 | 7450 |
| Control serum lot with a specified fructosamine concentration of 286 $\mu$mol/l | 266 | 265 | 280 |
| Control serum lot with a specified fructosamine concentration of 551 $\mu$mol/l | 532 | 519 | 554 |
| Calibrator lot with a specified fructosamine concentration of 479 $\mu$mol/l | 478 | 484 | 493 |

As can be seen on this table, none of the measured parameters shows a significant variation after one year of storage at 2°–8° C. After one year of storage at 24°–26° C., the calibration factor and the photometric linear response maximum concentration are stable, whereas the uricase activity shows a slight decrease and the absorption a slight increase: these minor changes do not affect the practical use of this reagent in tests, uricase being used in excess and the slight change of the absorption value having no effect on the kinetic measurement.

2) Stability under conditions of use.

Conditions of use were simulated by keeping first liquid reagent R1 in a bottle with a small opening allowing air exchange. Three of the above coefficients were measured, immediately after first opening of the bottle and after 8 weeks of storage at a temperature between 4° and 8° C. Results are shown in Table 2, hereafter.

TABLE 2

|  | Freshly opened | 8 weeks of use |
|---|---|---|
| Absorption at 550 nm | 0.006 | 0.007 |
| Linear response maximum concentration ($\mu$mol/l) | 1772 | 1769 |
| Calibration factor | 7508 | 7434 |

None of the measured parameters shows a significant variation after 8 weeks of storage under these conditions.

The first liquid reagent component, immediately after first opening of the bottle and after 8 weeks of storage at a temperature between 2° and 8° C., was used for measuring the fructosamine content of different plasma samples containing between 120 and 750 $\mu$mol/l of fructosamine, according to the method described in Example 3 1) b), mode C. 47 measurements were made for each of these solutions and the results were correlated. The regression straight line equation is: Y=1.00 X+3.00 (X and Y being respectively the values measured for the first liquid reagent, immediately after first opening of the bottle and after 8 weeks of storage at a temperature between 2° and 8° C.). There is no significant difference between these two solutions with a confidence interval of 99.5%.

The above described results show the excellent stability of the set of reagents of the invention under conditions of storage and of use.

EXAMPLE 3

Comparison Between the Method of the Present Invention and a Commercially Available Method of the Prior Art Three different modes of the method of the present invention were used for measuring the fructosamine content of plasma samples containing between 50 and 650 $\mu$mol/l of fructosamine and results were correlated to those obtained with the commercially available Fructosamine Plus method, used as reference method.

1) Description of the tests

All tests were carried out in a Cobas Mira analyser, using a reaction temperature of 37° C. and a spectrometric measurement at 550 nm.

a) Fructosamine Plus method

A commercial kit Fructosamine Plus (Roche) was used. One tablet containing NBT and uricase was dissolved in 20 ml of the buffer of pH 10.4 containing detergent.

200 $\mu$l of the reagent mixture were simultaneously mixed with 10 $\mu$l of the sample and 30 $\mu$l of water. The reaction rate was measured between 8.3 and 13.8 minutes.

b) Method of the invention

Mode A:

7 ml of the first liquid reagent (0.82 mmol/l NBT; 70 mmol/l potassium chloride; 70 mmol/l potassium phosphate buffer pH 7.5; 56 mmol/l Genapol X-80; 5.6 mmol/l sodium cholate; 4000 U/l uricase of Arthrobacter protophormiae) were mixed before use with 3 ml of the second liquid reagent (500 mmol/l potassium carbonate buffer pH 10.4)

200 µl of the reagent mixture were simultaneously mixed with 10 µl of the sample and 30 µl of water. The reaction rate was measured between 8.3 and 13.8 minutes.

Mode B:

The first and second liquid reagents, which had the same composition as in mode A, were used separately on the analyser.

140 µl of the first liquid reagent were simultaneously mixed with 60 µl of the second liquid reagent and 10 µl of the sample. The reaction rate was measured between 8.3 and 13.8 minutes.

Mode C:

The first liquid reagent (1.2 mmol/l NBT; 100 mmol/l potassium chloride; 100 mmol/l potassium phosphate buffer pH 7.5; 80 mmol/l Genapol X-80; 12 mmol/l sodium cholate; 4000 U/l uricase of Arthrobacter protophormiae) and the second liquid reagent (1500 mmol/l potassium carbonate buffer pH 10.4) were used separately on the analyser.

100 µl of the first liquid reagent were simultaneously mixed with 10 µl of the sample and 40 µl of water. After 3.3 min the reaction was started by adding 20 µl of the second reagent and 40 µl of water. The reaction rate was measured between 13.3 and 15.4 minutes.

2) Results

Results obtained using the method of the invention above described methods A, B and C were correlated to those obtained using the reference method. The number of measurements made and the slope a and the intercept b of the regression straight line Y=a X+b (Y being the value measured for the method according to the invention and X being the value measured for the reference method), as well as the Spearman rank correlation coefficient are shown in table 3 hereafter.

TABLE 3

|  | Method A | Method B | Method C |
|---|---|---|---|
| Number of measurements | 110 | 110 | 110 |
| Slope a | 1.03 | 1.02 | 1.03 |
| Intercept b (µmol/l of fructosamine) | −7.6 | −7.7 | −13.2 |
| Spearman rank correlation coefficient | 0.987 | 0.966 | 0.989 |

The above results show that each of the above described modes of the method of the invention has a very high degree of correlation with the reference method. The very stable set of reagents according to the invention will therefore also allow excellent clinical results.

I claim:

1. A kit of separate liquid reagent components for determining the fructosamine content in a blood sample comprising a first liquid reagent component which is at a substantially neutral pH and contains a neutral buffering agent, a tetrazolium salt at a concentration of 0.5 to 1.5 mmol/L, an enzyme with oxidizing activity which prevents non-specific reduction of the tetrazolium salt, and a detergent which removes turbidity; and a second liquid reagent component which is at a basic pH and contains a basic buffering agent.

2. A kit of claim 1 wherein the tetrazolium salt is nitro-blue tetrazolium.

3. A kit of claim 1 wherein the pH of the second liquid reagent component is from about 9 to about 12.5.

4. A kit of claim 1 wherein the pH of the second liquid reagent component is from about 10 to about 11 and the basic buffering agent is a carbonate buffer.

5. A kit of claim 1 wherein the pH of the first liquid reagent component is from about 7 to about 8.

6. A kit of claim 1 wherein the enzyme is uricase.

7. A kit of claim 1 wherein the detergent which removes turbidity is selected from an ionic or non-ionic detergent or a combination of an ionic detergent and a non-ionic detergent.

8. A kit of claim 7 wherein the ionic detergent is sodium cholate.

9. A kit of claim 7 wherein the non-ionic detergent is isotridecylpoly(ethylene-glycolether)n, where n is 8 to 12.

10. A kit of claim 7 wherein the detergent which removes turbidity additionally comprises a salt of a strong acid.

* * * * *